United States Patent [19]
Schraga

[11] Patent Number: 5,454,828
[45] Date of Patent: Oct. 3, 1995

[54] LANCET UNIT WITH SAFETY SLEEVE

[76] Inventor: Steven Schraga, 1841 NE. 146th St., North Miami, Fla. 33181

[21] Appl. No.: 213,953

[22] Filed: Mar. 16, 1994

[51] Int. Cl.⁶ ............................................... A61B 17/34
[52] U.S. Cl. ........................................... 606/181; 606/172
[58] Field of Search .................................... 606/181, 172

[56] References Cited

U.S. PATENT DOCUMENTS

| | | | |
|---|---|---|---|
| 55,775 | 6/1866 | Klee | 606/172 |
| 3,358,689 | 12/1967 | Higgins | 606/181 |
| 4,889,117 | 12/1989 | Stevens | 606/181 |
| 5,250,063 | 10/1993 | Abidin et al. | 606/167 |
| 5,312,354 | 5/1994 | Allen et al. | 606/172 X |
| 5,318,584 | 6/1994 | Lange et al. | 606/181 X |

*Primary Examiner*—Stephen C. Pellegrino
*Assistant Examiner*—Nancy Mulcare
*Attorney, Agent, or Firm*—Malloy & Malloy

[57] ABSTRACT

An improved single use lancet unit with a movable safety sleeve for shielding the sharp contaminated tip of a used lancet including means for fixedly securing the sleeve in its protective position. The lancet unit includes a lancet having a rod-shaped body disposed at one end in a lancet retaining member and a sterile sharp tip at the other end. The lancet unit includes a movable sleeve with an axial passageway therethrough sized to receive the lancet body segment which extends beyond the retaining member coaxially therein. The sleeve is movable longitudinally from an initial position for use of the lancet unit wherein the sharp tip of the lancet projects beyond the sleeve to a protective position wherein the sleeve surroundingly encloses and shields the contaminated tip of the used lancet unit. The lancet unit further includes a coupling member and a receiving opening which matingly engage to fixedly secure the sleeve in its protective position.

11 Claims, 2 Drawing Sheets

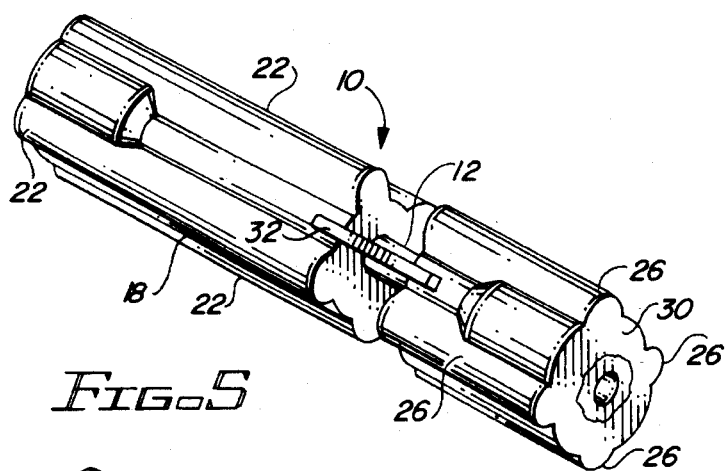
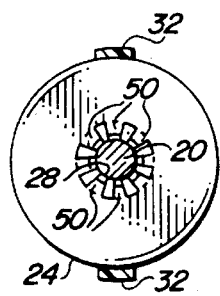
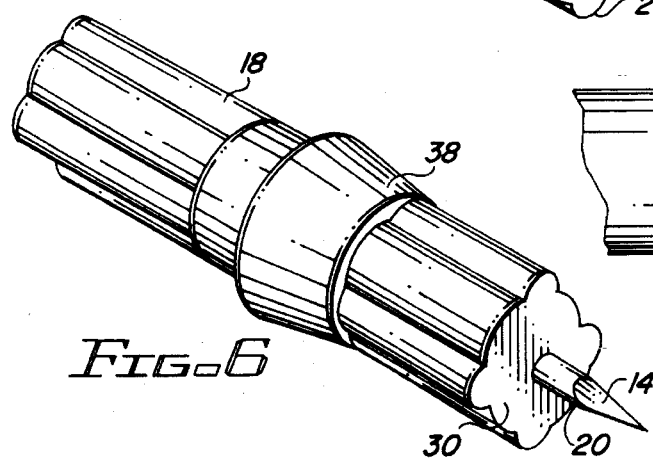
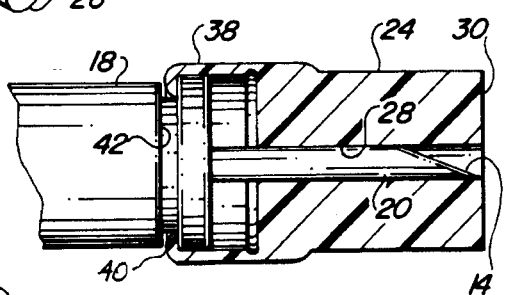
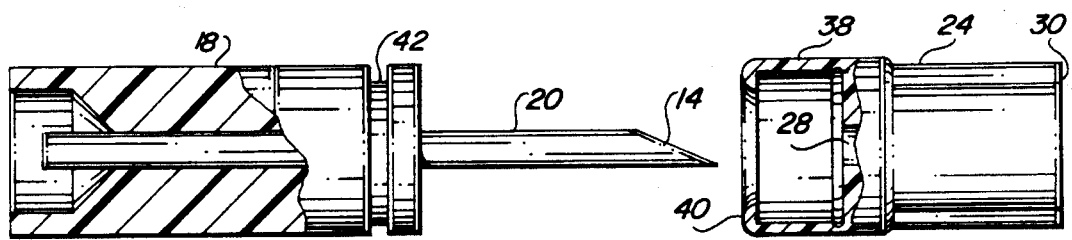
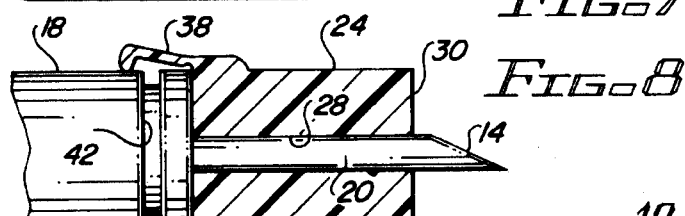
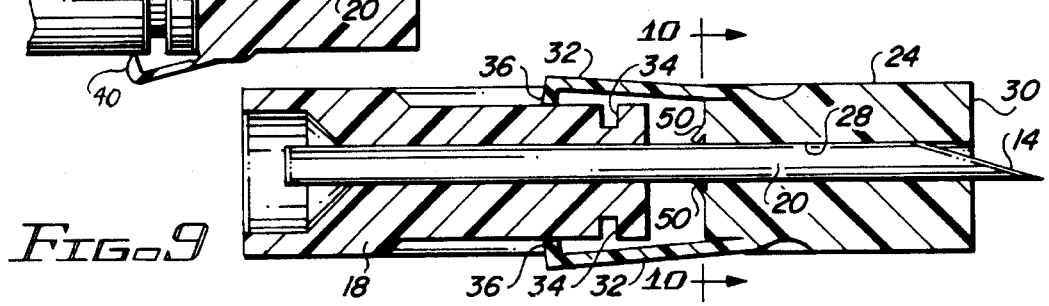

LANCET UNIT WITH SAFETY SLEEVE

BACKGROUND OF THE INVENTION

1. Field of the Invention

The present invention relates to an improved lancet unit having a safety sleeve that securely encloses and shields the contaminated sharp tip of a lancet. The safety sleeve is movable from an operative position which exposes the sterile lancet tip for use and into a fixed protective position which shields the lancet tip after use, and eliminates the risk of an accidental piercing of the user's fingers when the contaminated lancet is prepared for disposal.

2. Description of the Related Art

Lancets have long been employed to pierce or prick a patient's skin to provide a small outflow of blood that can be used in various medical tests. As described in expired U.S. Pat. No. 3,358,659 to Higgins, one type of lancet unit generally includes the lancet itself, usually an elongated metal rod with a sharp sterile tip, a plastic retainer member molded directly about the lancet and from which the sharp tip extends outwardly, and a removable cap connected to the plastic retainer member and in which the sterile tip is encased to prevent contamination prior to use.

Lancets are used both at home by the patient or in medical offices and hospitals by health care professionals, and can be used to prick the patient's skin either by manual penetration or in conjunction with a mechanical device into which the lancet unit is installed and then removed after use. In the home setting, most lancets are used by the patient with the mechanical device, which is designed to accept lancets of various sizes. In the medical office and hospital setting, lancets are often used manually in order to avoid the necessity of having to re-sterilize the mechanical device after each use. After the lancet unit has been used to prick the patient's skin, either manually or by means of the mechanical device, the sharp lancet tip is contaminated with the patient's blood. Because of the various high-risk, life-threatening diseases that are prevalent today throughout the world, used lancet units constitute an extremely hazardous form of waste. It is therefore essential that contaminated lancet tips be completely and securely shielded upon disposal of the used lancet units to prevent others, such as sanitation employees who routinely are unknowingly exposed to such types of hazardous waste, from being accidentally jabbed.

Thus, in the home use setting patients have been advised to discard used lancet units in a rigid container such as a coffee can or milk carton, but unfortunately many patients frequently fail to do this. In addition, although it is possible to dispose of a used lancet unit of the type described in the '659 patent by inserting the sharp contaminated tip back into the cap which was removed prior to use, this is generally not done. One reason for this is because the cap is fairly small and the hole in it is minuscule, so that the person attempting to recap the lancet unit is exposed to the risk of inadvertently jabbing himself with the contaminated lancet tip before it is finally inserted into the cap. Also, the cap can be lost or misplaced after being removed from the lancet unit prior to use, thereby precluding its replacement. Even if the lancet tip is replaced back into such a cap, however, there is a possibility that the cap can accidentally fall or be knocked off because the cap is not designed to be securely re-connected to the retaining member or the tip after the lancet has been used.

More recently, lancet units have been designed with protective caps that include a mouth, sized and adapted to fit securely over the end face of the lancet retainer member from which the tip extends, and a pocket into which the tip of a used lancet can be inserted and protectively enclosed. Although the enlarged mouth decreases the possibility that a person may accidentally jab himself when replacing this type of cap, the risk of such an occurrence still exists because the user's hand which grasps the cap is required to move in the direction of the sharp lancet tip in order to re-cap the lancet unit. Thus, if the user becomes momentarily distracted from the task, for example, the mouth of the cap may not be replaced precisely over the end face of the lancet retainer member and the user can still inadvertently jab himself with the contaminated lancet tip. In addition, a used lancet unit protected with such a cap might be mistaken for an unused unit.

The device of the present invention is designed to meet the need of providing a simple, easy to use protective cover that fixedly encloses and shields the sharp contaminated tip of a used lancet for disposal, while eliminating the risks that the user's hand will be accidentally jabbed when the cover is placed into its protective position or that a worker will be inadvertently jabbed during disposal of the lancet units.

SUMMARY OF THE INVENTION

The present invention is directed towards an improved single use lancet unit with a movable safety sleeve for shielding the sharp contaminated tip of a used lancet and means for fixedly securing the sleeve in its protective position. The lancet unit includes a lancet having a rod-shaped body with a sterile sharp tip. The lancet is at one end fixedly disposed in a lancet retaining member, with a segment of its body and the sharp tip extending outwardly beyond the retaining member. The lancet unit includes a movable sleeve with an axial passageway therethrough sized to receive the outwardly extending lancet body segment coaxially therein. The sleeve is movable longitudinally from an initial position for use of the lancet unit wherein the sharp tip of the lancet projects beyond the sleeve to a protective position wherein the sleeve surroundingly encloses and shields the contaminated tip of the used lancet unit. The lancet unit further includes means for fixedly securing the sleeve in its protective position.

It is an object of the present invention to provide an improved lancet unit with a safety sleeve that can be easily positioned by the user to protectively enclose and shield the sharp tip of a used lancet.

It is also an object of the invention to provide an improved lancet unit with a protective cover that is not easily lost or separated from the contaminated lancet tip which it shields and which can be manufactured cost-effectively.

Still another object of the invention is to provide an improved lancet unit with means for fixedly securing the safety sleeve in its protective position.

A further object of the present invention is to provide an improved lancet unit with a safety sleeve that can be moved into its protective position without the user accidentally jabbing himself.

Yet another object is to provide an improved lancet unit that can be disposed of safely after use without risk of further exposure to the contaminated lancet tip.

BRIEF DESCRIPTION OF THE DRAWINGS

For a fuller understanding of the nature of the present invention, reference should be had to the following detailed description of the presently preferred embodiment taken in conjunction with the accompanying drawings in which:

FIG. 5 is a perspective view of the lancet unit with the sleeve secured in its protective position.

FIG. 6 is a perspective view of the lancet unit in its operative position, showing an alternative embodiment of means for securing the sleeve in its protective position.

FIG. 7 is an exploded cross-sectional side view of the lancet unit shown in FIG. 6.

FIG. 8 is a cross-sectional side view of a portion of the lancet unit shown in FIG. 6 in its operative position.

FIG. 9 is a cross-sectional side view of the lancet unit of the present invention modified to include means for reducing the length of the lancet tip that is exposed for penetration.

FIG. 10 is a vertical sectional view taken along the line 10—10 of FIG. 9.

FIG. 11 is a cross-sectional side view of a portion of the lancet unit shown in FIG. 6, with the sleeve secured in its protective position.

DETAILED DESCRIPTION OF THE PREFERRED EMBODIMENT

Figure 1:
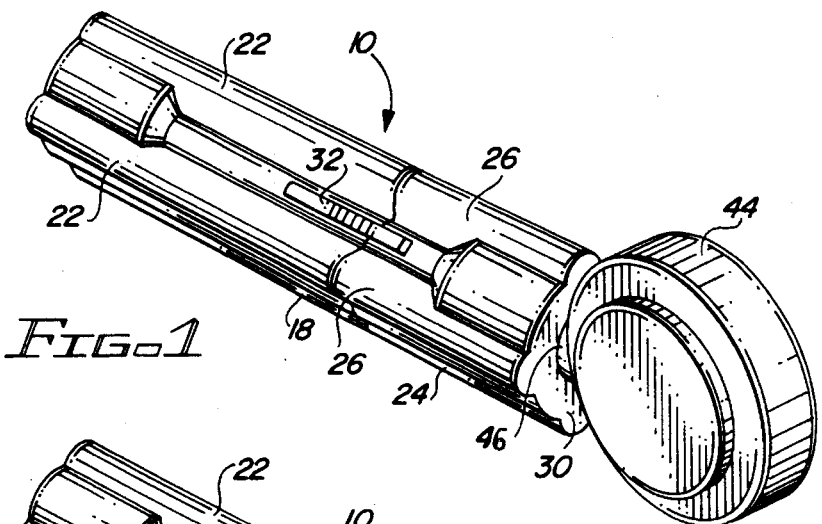
FIG. 1 is a perspective view of the lancet unit prior to use with a cap enclosing the tip.
Figure 1A:
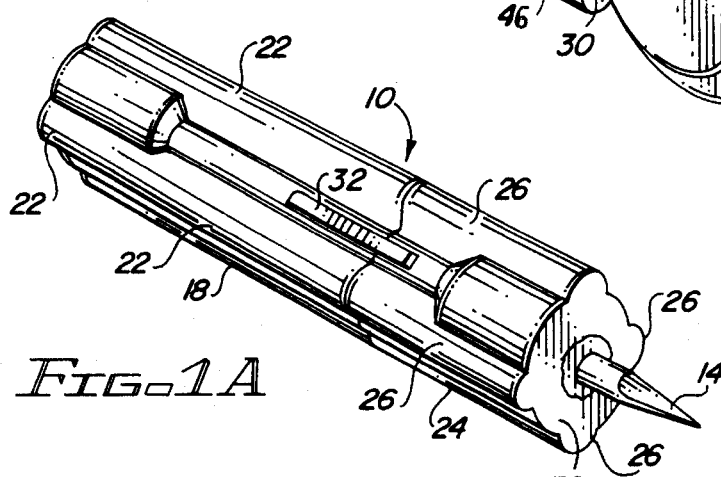
FIG. 1A is a perspective view of the lancet unit in its operative position with the sterile tip of the lancet exposed.
Figure 2:
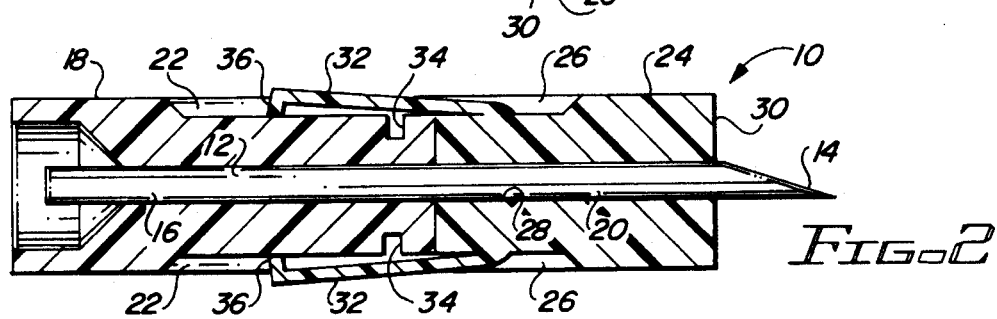
FIG. 2 is a cross-sectional side view of the lancet unit in its operative position.

Referring to the drawings, there is shown in FIGS. 1A and 2 a preferred embodiment of the lancet unit 10 which includes a metal lancet having an elongated rod member 12 and a sterile sharp tip 14. One segment 16 of the rod member 12 is fixedly disposed within a plastic lancet retaining member 18 that has been molded directly around it. A second segment 20 of the rod member 12 and the lancet tip 14 extend beyond the retaining member 18. The retaining member 18 has a generally tubular body which is preferably of a generally cylindrical shape. The body of the retaining member 18 may include a plurality of ribs to prevent twisting of the lancet unit 10 within a mechanical device, to facilitate holding the retaining member 18 between a user's fingers, or to act as reinforcing support in the manufacture of the unit such as in plastic injection molds. As seen in FIG. 1A, the preferred embodiment includes four longitudinally formed ribs 22 projecting radially outward and spaced angularly at 90°.

The lancet unit 10 includes a movable safety sleeve 24 with a generally tubular body that is preferably of a cylindrical shape corresponding in size and configuration to the body of the retaining member 18. The body of the sleeve 24 may also include a plurality of ribs to facilitate grasping the sleeve 24 between a user's fingers. In the preferred embodiment, the sleeve 24 has four longitudinally formed ribs 26 projecting radially outward and spaced angularly at 90°. As seen in FIG. 2, the sleeve 24 has an axial passageway 28 extending completely therethrough which is sized and configured to receive the second segment 20 of the lancet rod member 12 coaxially therein. The axial passageway 28 loosely frictionally engages the second rod segment 20, requiring the user to exert a longitudinally-directed force to slide the sleeve 24 along the second rod segment 20. The body of the sleeve 24 includes an outer end wall 30 as shown in FIG. 1A for stopping engagement against a patient's skin when the lancet unit 10 is used manually. The sleeve 24 is movable from an initial position, illustrated in FIGS. 1A and 2, for use of the lancet unit 10 in which the sterile tip 14 projects beyond the outer end wall 30, to a second protective position shown in FIGS. 4 and 5, in which the contaminated tip 14 of the used lancet unit 10 is surroundingly enclosed and shielded by the sleeve 24.

Figure 3:
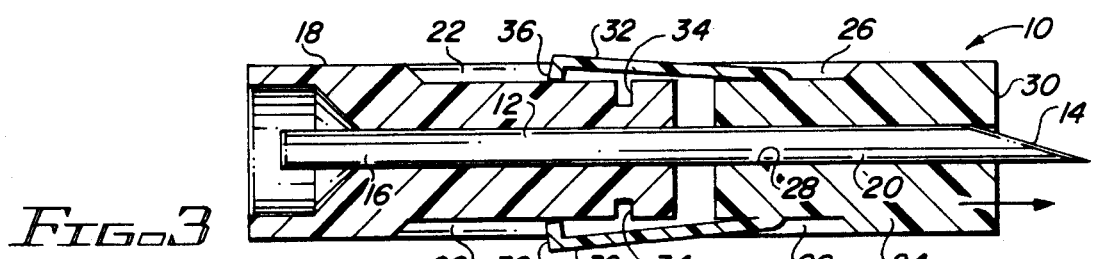
FIG. 3 is a cross-sectional side view of the lancet unit showing the sleeve being moved in the direction of the arrow into its protective position.
Figure 4:
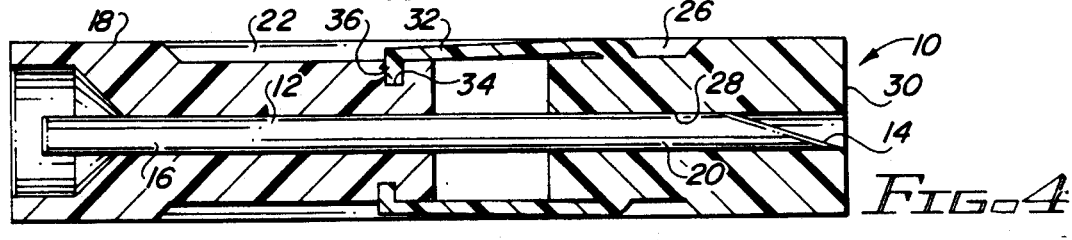
FIG. 4 is a cross-sectional side view of the lancet unit with the sleeve secured in its protective position surroundingly shielding the lancet tip.

The lancet unit 10 further includes means for fixedly securing the sleeve 24 in its second protective position. It can be appreciated that such means could be defined by the axial passageway 28 being sized to tightly engage the second rod segment 20 such that only a predetermined longitudinally-directed force of sufficiently large magnitude would be capable of effecting movement of the sleeve 24. In the preferred embodiment of the lancet unit 10, the securing means includes at least one coupling member attached to an exterior surface of the sleeve 24 and at least one receiving opening disposed within the body of the retaining member 18. As shown in FIGS. 2 through 5, the coupling member comprises a pair of oppositely disposed elongated arms 32 extending longitudinally over the body of the retaining member 18. Each arm 32 includes a latching segment 36 that projects radially inwardly and, in the initial position of the sleeve 24 shown in FIG. 2, is biased against an exterior surface of the retaining member 18. The receiving opening comprises a pair of oppositely disposed slots 34 in the body of the retaining member 18 that are configured to companionately receive the corresponding latching segments 36 therein. When the sleeve 24 is moved into its protective position, as seen in FIG. 4, both latching segments 36 matingly engage their corresponding slots 34 whereby the sleeve 24 is fixedly secured in that position.

In an alternative embodiment illustrated in FIGS. 6–8, the receiving opening of the securing means can be an annular channel 42 disposed within the body of the retaining member 18. The coupling member of this embodiment will be an annular skirt 38 attached to an exterior surface of the sleeve 24 and extending over the body of the retaining member 18. The skirt includes an annular lip 40 projecting radially inwardly that is biased against the body of the retaining member 18 in the initial position of the sleeve 24 and which is configured to be companionately received within the channel 42. When the sleeve 24 is moved into its protective position, as shown in FIG. 11, the lip 40 matingly engages the channel 42 thereby holding the sleeve 24 securely in that protective position and preventing further movement. In a further embodiment (not shown), the receiving opening of the securing means can be a notch on the second rod segment 20 of the lancet and the coupling member can be a protrusion formed on an internal surface of the axial passageway 28. The protrusion would be structured and disposed to matingly engage the notch when the sleeve 24 is moved into its protective position, again causing the sleeve 24 to be held fixedly in that position.

As shown in FIG. 1, the lancet unit 10 preferably includes a removable cap 44 in which the sterile lancet tip 14 is sealably enclosed prior to use. The cap 44 can be integrally formed with the sleeve 24 by a frangible neck section 46 that can be easily broken and the cap 44 removed by twisting the cap 44 relative to the sleeve 24. The lancet unit 10 of the present invention may also include means for adjusting the depth that the lancet tip 14 will penetrate into the patient's skin. As illustrated in FIGS. 9 and 10, this adjusting means comprises a plurality of fingers 50 structured and disposed around the circumference of an internal surface of the axial passageway 28 at the end of the sleeve 24 opposite the outer end wall 30. The fingers 50 are initially disposed radially inwardly with their distal ends in frictional contact with the second rod segment 20 and are bendable at their proximal ends such that when the sleeve 24 is moved in a forward direction away from the retaining member 18, the fingers 50 are drawn out of the sleeve 24 into a truncated conical configuration. When the fingers 50 have been fully drawn out of the sleeve 24, as shown in FIG. 9, there is a reduced length of the tip 14 exposed for penetration into the patient's skin, and the conical configuration of the fingers 50 bears against the second rod segment 20 so as to prevent the sleeve 24 from being moved backwards towards the retaining member 18 to re-expose an increased length of the tip 14. In this manner, and depending upon the size of the fingers 50, the length of the lancet tip 14 that is exposed for penetration into the patient's skin can be effectively reduced. Because such adjusting means does not prevent continued movement of the sleeve 24 in the forward direction away from the retaining member 18 and does not fixedly secure the sleeve 24 in place, the adjusting means is preferably formed on the lancet unit 10 in conjunction with the securing means of the present invention.

As indicated, the lancet unit 10 of the present invention can be used manually to penetrate a patient's skin or preferably together with a mechanical delivery device into which the lancet unit 10 is initially loaded and then removed after use. In both cases, the used lancet unit 10 is readied for disposal by holding the retaining member 18 between the fingers of one hand, grasping the sleeve 24 between the fingers of the other hand, and as shown in FIG. 3, sliding the sleeve 24 in the direction shown by the arrowed line to protectively shield the sharp contaminated tip 14 until the latching segments 36 engage the slots 34 in the retaining member 18. As seen in FIG. 4, once the latching segments 36 are companionately received into their respective corresponding slots 34, further movement of the sleeve 24 is prevented and the sleeve 24 will be held securely in its protective position, surroundingly enclosing and shielding the lancet tip 14 from further exposure. It will therefore be understood that in this protective position, the improved lancet device of the present invention can be readily disposed of without any need to recap the sharp contaminated tip, which recapping as previously explained can often result in confusion and mistake as to whether a lancet device is unused.

It is also readily understood that the foregoing manner of positioning the sleeve 24 to shield the used lancet tip 14 does not require a user's hand to move in the perilous direction, i.e., on a path towards collision with the contaminated tip 14 which might result in a prick to the finger or hand, but instead in the opposite direction as shown by the arrowed line in FIG. 3, which effectively eliminates the possibility of accidental jabbing when the sleeve 24 is moved into its protective position. Moreover, the used lancet unit 10 of the present invention is able to be disposed of safely because the operation of the securing means to fixedly maintain the sleeve 24 in its protective position eliminates any risk of the sleeve 24 being moved inadvertently to re-expose the contaminated tip 14.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An improved lancet unit comprising:
    (a) a lancet retaining member having a first and a second end;
    (b) a lancet comprising an elongated rod member with a sterile sharp tip, said rod member having a first segment and a second segment, said first rod segment being fixedly disposed within said retaining member and said second rod segment extending beyond said second end of said lancet retaining member;
    (c) a movable sleeve having a forward end, a rear end, and an axial passageway extending therebetween, said axial passageway being sized to receive said second rod segment coaxially therein, said sleeve rear end and said second end of said lancet retaining member being structured and disposed to confront each other in stopping abutment such that said sleeve is prevented from entering within an interior of said lancet retaining member;
    (d) said sleeve being supported on said second rod segment and movable longitudinally from an initial position wherein said sleeve rear end and said second end of said lancet retaining member are disposed in stopping abutment and said lancet tip projects outwardly beyond said sleeve forward end to a second protective position wherein said sleeve and said lancet retaining member are disposed in separated relation and said lancet tip is surroundingly enclosed and shielded by said sleeve; and
    (e) means structured and disposed on the lancet unit for fixedly securing said sleeve in said second position.

2. An improved lancet unit as recited in claim 1 wherein said securing means comprises a coupling member configured and located to matingly engage a receiving opening upon movement of said sleeve into said second position.

3. An improved lancet unit as recited claim 2 wherein said coupling member has a distal end and a proximal end, said proximal end being attached to an exterior surface of said sleeve, and said receiving opening being disposed within said retaining member.

4. An improved lancet unit as recited in claim 2 wherein said coupling member has a distal end and a proximal end, said proximal end being attached to an exterior surface of said retaining member, and said receiving opening being disposed within said sleeve.

5. An improved lancet unit as recited in claims 3 or 4 wherein said coupling member comprises an arm having a latching segment formed at said distal end, and said receiving opening comprises a slot structured and disposed to receive said latching segment companionately therein.

6. An improved lancet unit as recited in claims 3 or 4 wherein said coupling member comprises an annular skirt having a lip formed at said distal end, and said receiving opening comprises an annular channel structured and disposed to receive said lip companionately therein.

7. An improved lancet unit as recited in claim 2 wherein said coupling member is formed on an interior surface of said axial passageway and said receiving opening is disposed within said second rod segment.

8. An improved lancet unit comprising:
    (a) a lancet retaining member having a first and a second end;
    (b) a lancet comprising an elongated rod member with a sterile sharp tip, said rod member having a first segment and a second segment, said first rod segment being fixedly disposed within said retaining member and said second rod segment extending beyond said second end of said lancet retaining member;

(c) a movable sleeve having a forward end, a rear end, and an axial passageway extending therebetween, said axial passageway being sized to receive said second rod segment coaxially therein, said sleeve rear end and said second end of said lancet retaining member being structured and disposed to confront each other in stopping abutment such that said sleeve is prevented from entering within an interior of said lancet retaining member;

(d) said sleeve being supported on said second rod segment and movable longitudinally from an initial position wherein said lancet tip projects outwardly beyond said sleeve forward end to a second protective position wherein said sleeve and said lancet retaining member are disposed in separated relation and said lancet tip is surroundingly enclosed and shielded by said sleeve; and (e) means on the lancet unit for adjusting the length of said lancet tip exposed for penetration into a patient's skin, said adjusting means being structured and disposed to provide unidirectional movable engagement of said sleeve relative to said second rod segment, whereby said sleeve can be moved in a direction way from said retaining member in order to reduce the exposed portion of said lancet tip but cannot subsequently be moved in an opposite direction to increase said exposed portion of said lancet tip.

9. An improved lancet unit as recited in claim 8 wherein said adjusting means comprises a plurality of fingers disposed about a circumference of an internal surface of said axial passageway at said rear end of said sleeve, each of said fingers having a distal end and a proximal end, said fingers being positioned radially inwardly with said distal ends thereof contacting said second rod segment and being bendable at said proximal ends thereof, said fingers being structured so that when sleeve is moved in a direction away from said retaining member, said fingers are drawn out of said sleeve into a truncated conical configuration that prevents movement of said sleeve in an opposite direction.

10. An improved lancet unit as recited in claim 8 further comprising means structured and disposed on the lancet unit for fixedly securing said sleeve in said second position.

11. An improved lancet unit as recited in claim 1 further comprising a removable solid cap for preventing exposure of said lancet tip prior to use of said lancet unit, said cap being removably attached to said sleeve, said cap being structured and disposed to surroundingly enclose said lancet tip in said initial position.

* * * * *